(12) United States Patent  
Hiraoka

(10) Patent No.: US 8,871,522 B2  
(45) Date of Patent: Oct. 28, 2014

(54) METHOD FOR DETECTING HYDROGEN PEROXIDE

(75) Inventor: Kenzo Hiraoka, Kofu (JP)

(73) Assignee: University of Yamanashi, Yamanashi (JP)

( * ) Notice: Subject to any disclaimer, the term of this patent is extended or adjusted under 35 U.S.C. 154(b) by 599 days.

(21) Appl. No.: 13/210,166

(22) Filed: Aug. 15, 2011

(65) Prior Publication Data

US 2011/0300636 A1     Dec. 8, 2011

Related U.S. Application Data

(63) Continuation-in-part of application No. PCT/JP2010/052392, filed on Feb. 10, 2010.

(30) Foreign Application Priority Data

Feb. 16, 2009    (JP) .................................. 2009-032466

(51) Int. Cl.
    *G01N 33/00*      (2006.01)
    *H01J 27/02*      (2006.01)
    *H01J 49/14*      (2006.01)

(52) U.S. Cl.
    CPC .......... *H01J 27/028* (2013.01); *G01N 33/0036* (2013.01); *H01J 27/026* (2013.01); *H01J 49/145* (2013.01)
    USPC ........... 436/135; 250/281; 250/282; 250/288; 436/173

(58) Field of Classification Search
    USPC .................... 250/281–282, 288; 436/135, 173
    See application file for complete search history.

(56) References Cited

FOREIGN PATENT DOCUMENTS

JP       2004-85374 A     3/2004

OTHER PUBLICATIONS

Cody, R. B. et al, Analytical Chemistry 2005, 77, 2297-2302.*
de Petris, G. et al, International Journal of Mass Spectrometry 2006, 249-250, 311-316.*
Blanksby, S. J. et al, Angewandt Chemie International Edition 2007, 46, 4948-4950.*
Song, L. et al, Journal of the American Society for Mass Spectrometry 2007, 18, 1789-1798.*
Benjamin M. Messer, et al., "computational and experimental studies of chemical ionization mass spectrometric detection techniques for atmospherically relevant peroxides", International Journal of Mass Spectrometry, vol. 197, Feb. 29, 2000. p. 219-235.
Christopher D. Cappa and Matthew J. Elrod, "A computational investigation of the electron affinity of CO3 and thermodynamic feasibility of CO3- (H2O) n +ROOH reactions", Phys. Chem. Chem. Phys., vol. 3, No. 15, 2001, p. 2986-2994.

(Continued)

*Primary Examiner* — Arlen Soderquist
(74) *Attorney, Agent, or Firm* — Birch, Stewart, Kolasch & Birch, LLP

(57) ABSTRACT

The presence of hydrogen peroxide vapor is detected with high sensitivity. Oxygen molecules in the air are ionized by electrons generated by a discharge plasma, thereby producing an oxygen molecule negative ion $O_2^-$. The oxygen molecule negative ion $O_2^-$ produced is supplied to a space in which a hydrogen peroxide molecule $H_2O_2$ is to be detected. If a hydrogen peroxide molecule $H_2O_2$ is present, a cluster ion $O_2^-(H_2O_2)$ of the oxygen molecule negative ion $O_2^-$ and hydrogen peroxide molecule $H_2O_2$ is produced. The hydrogen peroxide molecule $H_2O_2$, therefore, can be detected by mass spectrometry. Other gas-phase negative ions such as chloride ion $Cl^-$ can be used besides the oxygen molecule negative ion $O_2^-$.

4 Claims, 3 Drawing Sheets

(56) References Cited

OTHER PUBLICATIONS

Diedrich Harms, et al., "Selective determination of hydrogen peroxide by adduct formation with a dinuclear iron (III) complex and flow injection analysis/tandem mass spectrometry", Analyst, vol. 127, No. 11, 2002, p. 1410-1412.

H. Huang, P.K. Dasgupta "Renewable liquid film-based electrochemical sensor for gaseous hydroperoxides" Talanta 44 (1997) 605-615.

International Search Report, PCT/JP2010/052392, Mar. 16, 2010.

Thomas Reiner, et al., "Improved atmospheric trace gas measurements with an aircraft-based tandem mass spectrometer: Ion identification by mass-selected fragmentation studies", J Geophys Res, vol. 103, No. D23, 1998, p. 31309-31320.

Toshihiro Fujii et al., "H2O2+ no Kenshutsu", Annual Conference on Mass Spectrometry, Book of Abstracts, 2001, pp. 262 to 263.

* cited by examiner

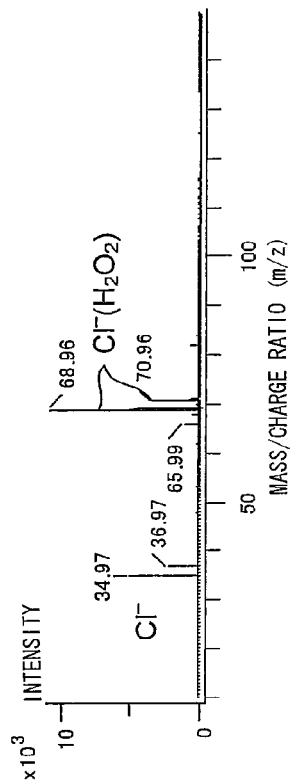
Fig. 3A (I)
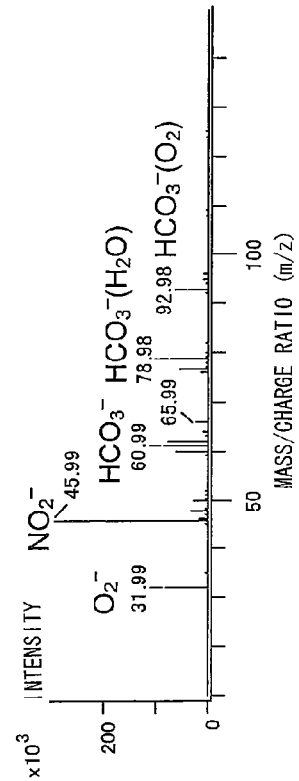
Fig. 3C (III)
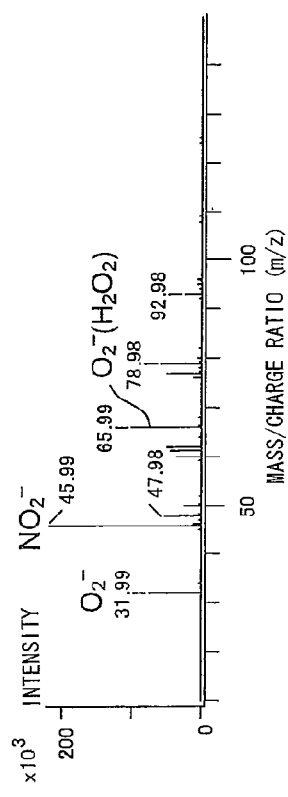
Fig. 3B (II)
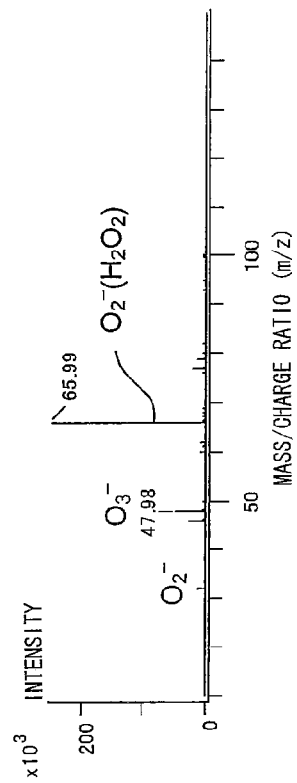
Fig. 3D (IV)

METHOD FOR DETECTING HYDROGEN PEROXIDE

CROSS REFERENCE TO RELATED APPLICATIONS

This application is a Continuation-In-Part of PCT International Application No. PCT/JP2010/052392 filed on Feb. 10, 2010, which claims priority under 35 U.S.C. 119(a) to Patent Application No. 2009-032466 filed in Japan, on Feb. 16, 2009. The entire contents of all of the above applications is hereby incorporated by reference into the present application.

BACKGROUND OF THE INVENTION

1. Field of the Invention

This invention relates to a method and apparatus for detecting hydrogen peroxide.

2. Description of the Related Art

Several methods of detecting hydrogen peroxide, which is contained in a solution, or gaseous hydrogen peroxide have already been proposed. For example, there is the following literature:

Japanese Patent Application Laid-Open No. 2004-85374
H. Huang, P. K. Dasgupta "Renewable liquid film-based electrochemical sensor for gaseous hydroperoxides" Talanta 44 (1997) 605-615.

However, a highly sensitive method of detecting gaseous hydrogen peroxide ions using mass spectrometry has not been proposed at all. The reason is that almost no parent (positive) ion $H_2O_2^+$ is produced. Even if such ions are produced, they readily decompose and are hindered by a signal ascribable to water vapor in the air, and detection is difficult.

SUMMARY OF THE INVENTION

An object of the present invention is to arrange it so that hydrogen peroxide can be detected through a simple operation.

A further object of the present invention is to arrange it so that hydrogen peroxide can be detected with high sensitivity.

A method of detecting hydrogen peroxide according to the present invention comprises the steps of: generating a gas-phase negative ion; supplying the generated gas-phase negative ion to a reaction space for clustering with a hydrogen peroxide molecule $H_2O_2$; and introducing the ions inside the clustering reaction space to an analyzing apparatus and detecting at least whether or not a cluster ion of the gas-phase negative ion and the hydrogen peroxide molecule $H_2O_2$ is present, thereby detecting at least whether or not hydrogen peroxide is present.

An apparatus for detecting hydrogen peroxide according to the present invention comprises: means for generating a gas-phase negative ion; means for supplying the generated gas-phase negative ion to a reaction space for clustering with a hydrogen peroxide molecule $H_2O_2$; and an analyzing apparatus to which the ions inside the clustering reaction space are introduced for detecting at least whether or not a cluster ion of the gas-phase negative ion and the hydrogen peroxide molecule $H_2O_2$ is present, thereby detecting at least whether or not hydrogen peroxide is present.

In one embodiment, the gas-phase negative ion is an oxygen molecule negative ion $O_2^-$, and a cluster ion $O_2^-(H_2O_2)$ comprising the oxygen molecule negative ion $O_2^-$ and hydrogen peroxide molecule $H_2O_2$ is detected in the analyzing apparatus.

In another embodiment, the gas-phase negative ion is a chloride ion $Cl^-$, and a cluster ion $Cl^-(H_2O_2)$ is detected in the analyzing apparatus.

Another gas-phase negative ion which forms a cluster ion with a hydrogen peroxide molecule $H_2O_2$ can be used besides an oxygen molecule negative ion $O_2^-$ and a chloride ion $Cl^-$.

If a vapor of hydrogen peroxide $H_2O_2$ is inside (or is being supplied to) the clustering reaction space, it reacts with the gas-phase negative ion and a cluster ion of the gas-phase negative ion and hydrogen peroxide molecule $H_2O_2$ is formed (generated). The cluster ion thus generated is introduced to the analyzing apparatus and at least the presence thereof (and relative amount or absolute amount, depending upon the analyzing apparatus) is detected. This makes it possible to detect the presence of hydrogen peroxide $H_2O_2$ and the amount thereof.

The gas-phase negative ion and the cluster ion can be generated under atmospheric pressure or reduced pressure.

As for a detailed description of a case where an oxygen molecule ion $O_2^-$ is used as the gas-phase negative ion, a method of detecting hydrogen peroxide using the oxygen molecule ion $O_2^-$ according to the present invention comprises the steps of: generating an oxygen molecule negative ion $O_2^-$; supplying the generated oxygen molecule negative ion $O_2^-$ to a space (clustering reaction space) in which a hydrogen peroxide molecule $H_2O_2$ is to be detected; introducing the ions inside this space to an analyzing apparatus and detecting at least whether or not a cluster ions $O_2^-(H_2O_2)$ comprising the oxygen molecule negative ion $O_2^-$ and the hydrogen peroxide molecule $H_2O_2$ is present, thereby detecting at least whether or not hydrogen peroxide is present.

An apparatus for detecting hydrogen peroxide using an oxygen molecule negative ion $O_2^-$ according to the present invention comprises: means for generating an oxygen molecule negative ion $O_2^-$; means for supplying the generated oxygen molecule negative ion $O_2^-$ to a space (clustering reaction space) in which a hydrogen peroxide molecule $H_2O_2$ is to be detected; and an analyzing apparatus to which the ions inside this space are introduced for detecting at least whether or not a cluster ion $O_2^-(H_2O_2)$ between the oxygen molecule negative ion $O_2^-$ and the hydrogen peroxide molecule $H_2O_2$ is present, thereby detecting at least whether or not hydrogen peroxide is present.

If a vapor of hydrogen peroxide $H_2O_2$ is inside (or is being supplied to) the clustering reaction space, it reacts with the oxygen molecule negative ion $O_2^-$ and a cluster ion $O_2^-(H_2O_2)$ of the oxygen molecule negative ion $O_2^-$ and hydrogen peroxide molecule $H_2O_2$ is formed (generated). The cluster ion $O_2^-(H_2O_2)$ thus generated is introduced to the analyzing apparatus and at least the presence thereof (and relative amount or absolute amount, depending upon the analyzing apparatus) is detected. This makes it possible to detect the presence of hydrogen peroxide $H_2O_2$ and the amount thereof.

Since the generation of oxygen molecule negative ions and the generation of cluster ions is possible even in the atmosphere, the generated cluster ions, for example, can be introduced from the atmosphere into a vacuum via an ion sampling orifice and detected by a mass spectrometer (or detector of an ion drift tube).

Since the negative ion $O_2^-$ is generated beforehand as the reaction ion and is bound to the $H_2O_2$ molecule and detected as a cluster ion, this is a very gentle ionizing method and fragment ions are not produced. Further, even if water vapor mixes in, ion detection is almost unaffected. The reason for this is that since the bonding energy of $O_2^-(H_2O_2)$ is very large in comparison with $O_2^-(H_2O)$, almost no $O_2^-(H_2O)$ is produced on the condition that $H_2O_2$ is present.

The generation of oxygen molecule negative ions can be carried out by the generation of electrons, by way of example. That is, electrons are produced, oxygen molecules in the air are ionized by the generated electrons and the oxygen molecule negative ion $O_2^-$ is generated. Other gas-phase negative ions also can be generated by bonding with electrons.

Electrons can be produced by an electrical discharge under atmospheric pressure or reduced pressure (several Torr or higher). A barrier discharge, atmospheric-pressure DC discharge, high-frequency discharge or microwave discharge, etc., can be utilized as the electrical discharge. Any type of discharge gas will suffice, such as a rare gas, oxygen, air or nitrogen.

In a case where an electrical discharge in a vacuum (under reduced pressure) is utilized, a high-frequency discharge (on the MHz order) or microwave discharge (on the GHz order), etc., can also be used. An electron emission from a radioactive isotope element can be utilized as well. In any case, generated electrons can be made to attach to oxygen molecules and the oxygen molecule negative ion $O_2^-$ and other gas-phase negative ions can be produced.

BRIEF DESCRIPTION OF THE DRAWINGS

FIGS. 2A to 2C are graphs illustrating examples of actually measured values in the embodiment shown in FIG. 1, in which FIG. 2A illustrates a change in intensity of all ions with time, FIG. 2B a change in intensity of $O_2^-(H_2O_2)$ with time and FIG. 2C a change in intensity of $Cl^-(H_2O_2)$ with time; and FIGS. 3A to 3D illustrate mass spectra at portions (I) to (IV) in the graphs of FIGS. 2A to 2C, in which FIG. 3A (I) illustrates a case where hydrogen peroxide was supplied at a slight distance, FIG. 3B (II) a case where hydrogen peroxide was supplied nearby, FIG. 3C (III) a case where hydrogen peroxide and carbon tetrachloride vapor were supplied, and FIG. 3D (IV) a case where the supply of hydrogen peroxide and carbon tetrachloride vapor was halted.

DESCRIPTION OF THE PREFERRED EMBODIMENTS

Figure 1:
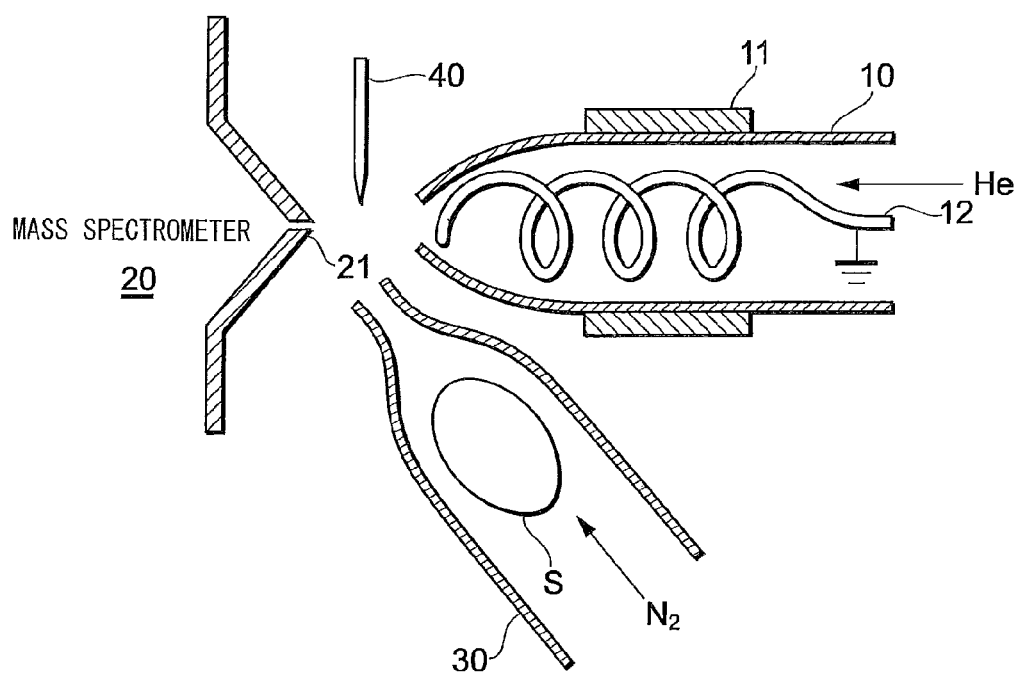
FIG. 1 illustrates the configuration of an embodiment of the present invention.

FIG. 1 is an embodiment relating to detection of hydrogen peroxide utilizing oxygen molecule negative ions. This embodiment utilizes barrier discharge in the generation of electrons and, hence, in the generation of oxygen molecule negative ions.

A barrier discharge tube 10 is brought close to (e.g., several millimeters or several centimeters distant from) an ion sampling orifice 21 (which has a small hole) of a mass spectrometer 20, and the distal end of the tube is arranged to oppose the orifice in the atmosphere. Helium (He) gas is passed as a discharge gas into the barrier discharge tube 10 from the base end thereof. The tip of the barrier discharge tube 10 is somewhat constricted. The interior of the mass spectrometer 20 is at a high degree of vacuum. A gaseous flow is therefore formed from the tip of the barrier discharge tube 10 toward the orifice 21. This flow portion is assumed to be the downstream portion of the barrier discharge tube. The upstream portion of the barrier discharge tube is inside the barrier discharge tube 10.

The barrier discharge tube 10 is a dielectric (e.g., glass) and the outer circumferential surface thereof is provided with an external electrode 11. An AC high voltage is impressed across the external electrode 11 and an internal electrode 12, described later. The internal electrode 12 is placed inside the barrier discharge tube 10 and is grounded. A barrier discharge is produced across the electrode 11 and 12. By passing the helium gas into the barrier discharge tube 10, a metastable excited species He+ having high energy is formed in the external side of the tip of the barrier discharge tube 10 (the downstream portion) and, as a result, atmospheric component gases ($N_2$, $O_2$, etc.) are ionized into excited ions and electrons are emitted. The electrons produced attach themselves to oxygen molecules $O_2$ and oxygen molecule negative ions $O_2^-$ are generated.

Cotton (a sample S) moistened with hydrogen peroxide solution is placed inside a sample supply tube (made of glass, for example) 30 and a carrier gas ($N_2$ gas, for example) is supplied to the supply tube 30 from the base thereof. Since the tip of the supply tube 30 is open and faces the downstream portion of the discharge tube, the hydrogen peroxide is supplied to the downstream portion of the discharge tube. The downstream portion of the discharge tube is a clustering reaction space.

If a vessel containing hydrogen peroxide is placed close to the downstream portion of the discharge tube (the clustering reaction space), the hydrogen peroxide $H_2O_2$, which is a vapor component, will be supplied to the downstream portion of the discharge tube even without passing a carrier gas. The oxygen molecule negative $O_2^-$ ion forms a strong bond with the hydrogen peroxide $H_2O_2$ and a cluster ion $O_2^-(H_2O_2)$ of the oxygen molecule negative ion and hydrogen peroxide is produced. The cluster ion is introduced from the orifice 21 to the interior of the mass spectrometer 20 and is detected by the mass spectrometer 20.

Since the $O_2^-$ ion need only be produced as the reaction ion at the downstream portion of the discharge tube, a rare gas can be used as the discharge gas, as a matter of course, and nitrogen, oxygen or air, etc, can also be used. The supply tube 30 and a supply of $N_2$ gas are not necessarily required, as mentioned above. Further, the downstream portion of the discharge tube is provided with a needle electrode 40. This is for removing impediment ions (background ions) that originate from barrier discharge plasma, and a positive or negative DC high voltage corresponding to the sign of the ions desired to be removed is applied thereto. The needle electrode 40 is not necessarily required. Further, the tip of the barrier discharge tube 10 need not necessarily be constricted, and the internal electrode 12 may be linear rather than coil-shaped as shown. Thus, there are a variety of modifications that can be made.

Since the generation of the cluster ion $O_2^-(H_2O_2)$ is a cluster-forming reaction consisting of an electrostatic interaction, it can be detected in the form of an adduct ion with $O_2^-$ (as a mass/charge ratio m/z value of 66 in the mass spectrometer 20) [m/z=65.99 in FIG. 3A (I) and FIG. 3B (II)] without causing the dissociation of readily decomposable $H_2O_2$.

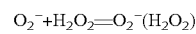

$$O_2^- + H_2O_2 = O_2^-(H_2O_2)$$

Since $O_2^-$ is readily generated from atmospheric oxygen as a core ion of the cluster ion, $H_2O_2$ can readily be detected without devising any particular contrivance for electrical discharge.

Since the ion signal $O_2^-(H_2O_2)$ appears very strongly even if an impurity ion (background) signal is present around m/z 66 of the cluster ion $O_2^-(H_2O_2)$, there is almost no possibility of wrong information. This is one outstanding point of the present invention.

A method of producing chloride ion $Cl^-$ at the downstream portion of the discharge tube is available as a method of positively confirming that the $O_2^-(H_2O_2)$ ion that appears at m/z 66 is a cluster ion of $O_2^-$ and $H_2O_2$. For example, if a slight amount of carbon tetrachloride gas $CCl_4$ is supplied to the downstream portion of the discharge tube, electrons (thermal electrons) produced by electrical discharge will react with the carbon tetrachloride and produce the chloride ion $Cl^-$.

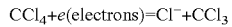

$$CCl_4 + e(\text{electrons}) = Cl^- + CCl_3$$

The chloride ion $Cl^-$ thus produced and the hydrogen peroxide give rise to the cluster ion $Cl^-(H_2O_2)$. Since the mass/charge ratio m/z value of this ion appears at 69 and 71 [m/z=68.96, 70.96 in FIG. 3C (III)], it can easily be confirmed that the adduct molecule is $H_2O_2$. This fact indicates that detection of hydrogen peroxide is possible by forming a cluster ion with a hydrogen peroxide molecule using the chloride ion $Cl^-$.

Figure 2A:
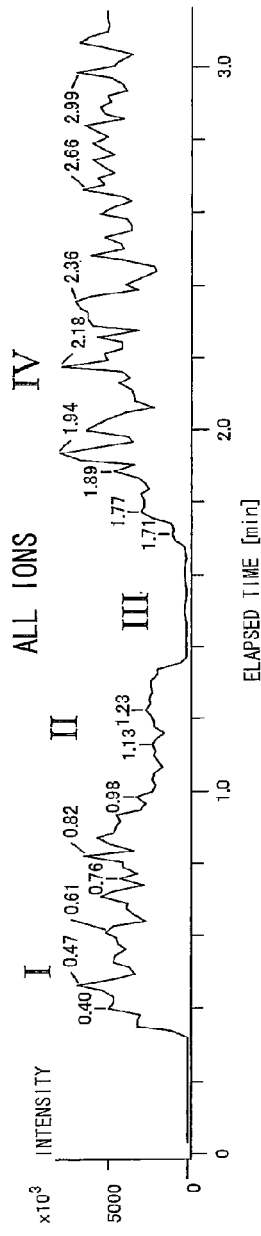
Figure 2B:
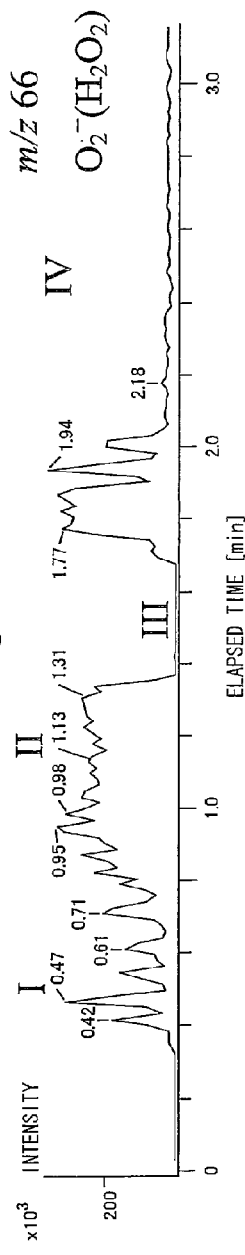
Figure 2C:
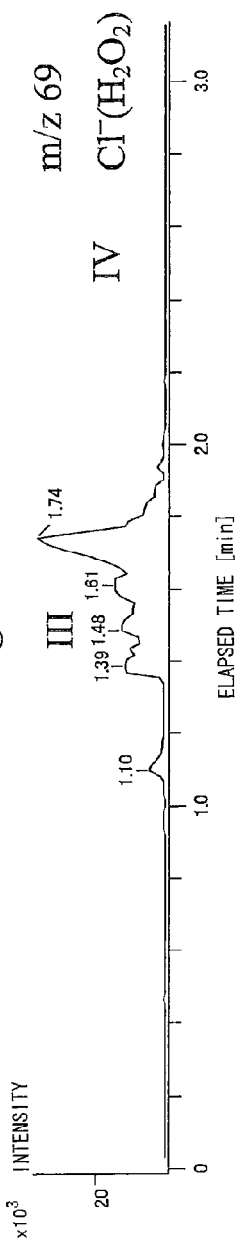

FIGS. 2A to 2C illustrate examples of actually measured values obtained using the apparatus shown in FIG. 1, in which FIG. 2A illustrates a change in all ion currents, FIG. 2B a change intensity of $O_2^-(H_2O_2)$ ion and FIG. 3C a change in intensity of $Cl^-(H_2O_2)$ ion. The portions indicated by I are for a case where a swab moistened with hydrogen peroxide was brought close to a position spaced 2 cm away from the center of the downstream portion of the discharge tube to one side thereof. The portions indicated by II are for a case where the swab was brought fairly close to the downstream portion of the discharge tube, the portions indicated by III are for a case where a swab moistened with carbon tetrachloride was brought close to the downstream portion of the discharge tube while the state II was maintained, and the portions indicated by IV are for a case where supply of hydrogen peroxide and carbon tetrachloride was halted. It will be understood that in the measurement of negative ion mode, $O_2^-(H_2O_2)$ was produced as the main product ion and that $O_2^-(H_2O_2)$ ions was transformed to $Cl^-(H_2O_2)$ ions by the supply of carbon tetrachloride $CCl_4$.

FIGS. 3A to 3D illustrate mass spectra actually measured in the cases I, II III, IV mentioned above. FIG. 3A (I) is a mass spectrum for a case where a swab containing a 30% $H_2O_2$ aqueous solution was brought close to a position spaced 2 cm away from the downstream portion of the discharge tube to one side thereof. The cluster ion $O_2^-(H_2O_2)$ was observed together with $O_2^-$, $NO_2^-$ ions, which are the original components of the atmosphere. FIG. 3A (II) is a mass spectrum for a case where the swab was brought fairly close to the downstream portion of the discharge tube. Most of the $O_2^-$ ion vanished and was transformed to $O_2^-(H_2O_2)$, which is a cluster ion with $H_2O_2$, and this was observed as the strongest ion. FIG. 3C (III) is for a case where carbon tetrachloride vapor was supplied to the downstream portion of the discharge tube in the state of FIG. 3B (II). It will be understood that the major portion of $O_2^-(H_2O_2)$ was transformed to $Cl^-(H_2O_2)$. In this case, the $Cl^-(H_2O_2)$ was measured as the strongest ion. Thus, it will be understood that by generating $O_2^-$ ions or $Cl^-$ ions using electrical discharge and generating $O_2^-(H_2O_2)$ or $Cl^-(H_2O_2)$ in the negative ion mode, hydrogen peroxide can be detected with high sensitivity. FIG. 3D (IV) is for a case where supply of the hydrogen peroxide and carbon tetrachloride was halted.

Hydrogen peroxide is the starting raw material of a peroxide explosive and establishing a method of detecting it is an urgent issue. In accordance with the present invention, the presence of a vessel of a hydrogen peroxide liquid can be detected with a high sensitivity. Hydrogen peroxide molecules are very strongly adsorptive, and in accordance with the present invention, it is possible to detect even trace components of a hydrogen peroxide solution that have been adsorbed onto the lid of a vessel. There are cases where detection is possible even if the lid of the vessel of hydrogen peroxide liquid is not opened. Since $O_2^-(H_2O_2)$ ions will be observed merely by bringing the vessel close to a spectrometer, the method according to the present invention is applicable not only to a simple mass spectrometer but also to an ion source that uses an ion drift tube presently available. The method according to the present invention is a highly sensitive detection method capable of selectively detecting only $H_2O_2$ without being influenced at all by the presence of water vapor, etc., in the atmosphere.

The detection of hydrogen peroxide can be performed using not only the oxygen molecule ion $O_2^-$ but also the chloride ion $Cl^-$ and other gas-phase negative ions.

What is claimed is:

1. A method of detecting hydrogen peroxide, comprising the steps of:
   generating an oxygen molecule negative ion $O_2^-$;
   supplying the generated oxygen molecule negative ion $O_2^-$ to a reaction space for clustering with a hydrogen peroxide molecule $H_2O_2$; and
   introducing the ions inside said clustering reaction space to an analyzing apparatus and detecting at least whether or not a cluster ion $O_2^-(H_2O_2)$ of the oxygen molecule negative ion $O_2^-$ and hydrogen peroxide molecule $H_2O_2$ is present, thereby detecting at least whether or not hydrogen peroxide is present.

2. A detection method according to claim 1, wherein electrons are generated, oxygen molecules in the air are ionized by the generated electrons and the oxygen molecule negative ion $O_2^-$ is generated.

3. A method of detecting hydrogen peroxide, comprising the steps of:
   generating a chloride negative ion $Cl^-$;
   supplying the generated chloride negative ion $Cl^-$ to a reaction space for clustering with a hydrogen peroxide molecule $H_2O_2$; and
   introducing the ions inside said clustering reaction space to an analyzing apparatus and detecting at least whether or not a cluster ion $Cl^-(H_2O_2)$ of the chloride negative ion $Cl^-$ and hydrogen peroxide molecule $H_2O_2$ is present, thereby detecting at least whether or not hydrogen peroxide is present.

4. A detection method according to claim 2, wherein electrons are generated by an electrical discharge under atmospheric pressure or reduced pressure.

* * * * *